United States Patent [19]

Sacherer et al.

[11] Patent Number: 4,834,234
[45] Date of Patent: May 30, 1989

[54] CONTAINER FOR TEST STRIPS

[75] Inventors: Klaus-Dieter Sacherer, Kirchheim; Erich Weiss, Mannheim, both of Fed. Rep. of Germany

[73] Assignee: Boehringer Mannheim GmbH, Mannheim, Fed. Rep. of Germany

[21] Appl. No.: 189,225

[22] Filed: May 2, 1988

[30] Foreign Application Priority Data

May 13, 1987 [DE] Fed. Rep. of Germany ....... 3715938

[51] Int. Cl.$^4$ ............................................ B65D 81/26
[52] U.S. Cl. .................................... 206/204; 215/227; 215/228
[58] Field of Search ......................... 206/204, 205, 569; 215/227, 228, 358, 359, 364; 312/31.1

[56] References Cited

U.S. PATENT DOCUMENTS

| 1,794,940 | 3/1931 | Zimmermann | 312/31.1 |
| 2,690,947 | 10/1954 | Roehrl | 312/31.1 |
| 3,028,036 | 4/1962 | Goll | 215/358 |
| 3,254,784 | 6/1966 | Lancesseur | 312/31.1 |

FOREIGN PATENT DOCUMENTS

| 0551178 | 10/1956 | Belgium | 312/31.1 |
| 0746040 | 7/1970 | Belgium | 215/228 |
| 2406558 | 8/1975 | Fed. Rep. of Germany | 215/227 |

*Primary Examiner*—Jimmy G. Foster
*Attorney, Agent, or Firm*—Felfe & Lynch

[57] ABSTRACT

The present invention provides a container for test strips for the analysis of body fluids, comprising a container body (2) with a circular removal opening (2a), a sealing surface (14) facing the axis (A) of the opening and a stopper (3) for the closure of the removal opening (2a) which has a cover plate (4), a hollow plug (7) attached thereto with an outwardly facing sealing beading (8), a drying agent cell (6) within the hollow plug and a support element (10) by means of which the plug is supported radially inwardly, wherein the support element is so constructed that it abuts the hollow plug in a region axially displaced away from the cover plate (4) with regard to the zenithal line (15) of the sealing beading (8), whereas axially, at the height of the sealing beading (8), between the inner side of the hollow plug and the drying agent cell, even when the stopper (3) is in a position permitting removal, an annular gap (9) is present so that the hollow plug (7) is radially inwardly elastically deformable in the region of the sealing beading (8).

8 Claims, 1 Drawing Sheet

CONTAINER FOR TEST STRIPS

FIELD OF THE INVENTION

The present invention is concerned with a container for test strips which serve for the analysis of body fluids.

The container comprises a container body with a circular removal opening, a sealing surface facing the axis of the opening and a stopper for the closure of the removal opening. The stopper has a cover plate, a hollow plug attached thereto with an outwardly facing sealing beading, a drying agent cell within the hollow plug and a support element by means of which the hollow plug is supported on its inner side.

BACKGROUND OF THE INVENTION

Test strips are used more and more for the analysis of body fluids and especially of blood and urine. Test strips are extraordinarily sensitive to moisture, which means that packaging standards for these are very high. In order to guarantee the necessary storage stability, the test strip containers must be practically completely sealed for a long period of time (at least two years). This tight sealing must also be maintained when the container is opened often (typically 50 times) in order to remove individual test strips.

In order to absorb the moisture which unavoidably gets in during the opening and closing of the test strip container, it must contain a sufficient amount of a drying agent. Nevertheless, the least possible amount of construction must be aimed for.

In spite of these requirements, the test strip packages must be easy to handle and must be easy to open and to reclose.

For a long time, test strip containers made of glass or metal and which were closed with a screw cap provided with a rubber seal were used almost exclusively. Such containers were expensive to make and their opening and reclosing was difficult.

Federal Republic of Germany patent specification No. 24 06 558 describes a test strip container and, in particular, an appropiate closure stopper of the above-described kind. A support element served to ensure sufficient sealing between the sealing beading and the associated sealing surface of the container. To accomplish this, the stopper is arranged axially at the same height as the sealing beading and, it is emphasized, an intermediate space is formed when the stopper is slackened between the support element, formed for example as a stabilizing ring, and the associated counter-surface of the hollow plug.

When a stopper constructed in this manner is introduced into the corresponding removal opening of the container body, the hollow plug is deformed comparatively easily until it lies against the support element, further elastic deformation being substantially prevented by the support element. In this way, one can achieve high pressing-on force of the sealing beading and thus good tightness.

Although it is possible, with the construction described in Federal Republic of Germany patent specification No. 24 06 558, to use closure stoppers of synthetic resin for the packaging of test strips, such packages are not satisfactory in every respect. After long storage, they are frequently difficult to open. High requirements are demanded of the tolerances of production, not only for the stoppers but also of the container bodies. Even in the case of very small deviations, it can happen that such containers develop leaks.

SUMMARY OF THE INVENTION

It is an object of the present invention to provide a container for test strips which satisfies the above-mentioned high requirements but, nevertheless, is easy to handle and to make.

This object is achieved via a container for test strips in which the support element is constructed so that it abuts the hollow plug in a region axially displaced away from the zenithal line of the sealing beading toward the interior of the container. The container has an annular gap axially, at the height of the sealing beading, and between the inner side of the hollow plug and the drying agent cell. The annular gap is present even when the stopper is inserted in the container, thereby closing the opening. By these means the hollow plug is radially inwardly elastically deformable in the region of the sealing beading.

Thus the present invention differs fundamentally from the invention described in Federal Republic of Germany patent specification No. 24 06 558 in that the support element is not arranged precisely where the sealing beading is present. On the contrary, according to the present invention, the abutment formed by the support element is displaced towards the interior of the container. A second abutment is formed in that the hollow plug is integrally cast on to the cover plate of the stopper. Between these two abutments, the hollow plug can be elastically deformed in such a manner that a definite, radial circumferential stress is produced, which remains almost constant for a long time.

According to the specific requirements, the stressing can be regulated via the wall thickness of the hollow plug and the thickness of the sealing beading.

Surprisingly, it has been shown that using such a construction outstanding long-time sealing is achieved in spite of the comparatively small pressing on force. Nevertheless, the stopper can, at any time, be removed and replaced relatively easily without jamming.

Further advantages are to be seen in that the stopper of the container according to the present invention can be produced, without problems, in one piece from an appropriate synthetic resin, for example polyethylene, that the construction is space-saving so that the stopper, in the case of a given amount of drying agent, can be made comparatively short and that comparatively little material is required for the production of the stopper. These advantages apply to an especial degree when the support element, according to a preferred embodiment, is constructed as a water-vapour permeable disc which, at the same time, covers the drying agent cell. A cardboard disc, such as is usually employed for covering the drying agent, is especially preferred.

According to another preferred embodiment, the removal opening is, narrowed with respect to the diameter of the sealing surface on at least a part of its circumference towards the edge of the opening. Thus, special advantages are provided in conjunction with the comparatively high elasticity of the stopper constructed according to the present invention. The stopper engages audibly and precisely into the closure position. Inadvertent slipping out of the stopper is prevented, even given great variations of the atmospheric pressure. Nevertheless, the container can be easily opened and closed. This is especially true when the narrowing on the edge of the opening is formed as a plurality of holding knops which are distributed around the edge of the opening.

BRIEF DESCRIPTION OF THE DRAWINGS

The present invention will now be described in more detail with reference to the embodiments illustrated schematically in the accompanying drawings, in which.

DETAILED DESCRIPTION OF THE PREFERRED EMBODIMENTS

Figure 1:
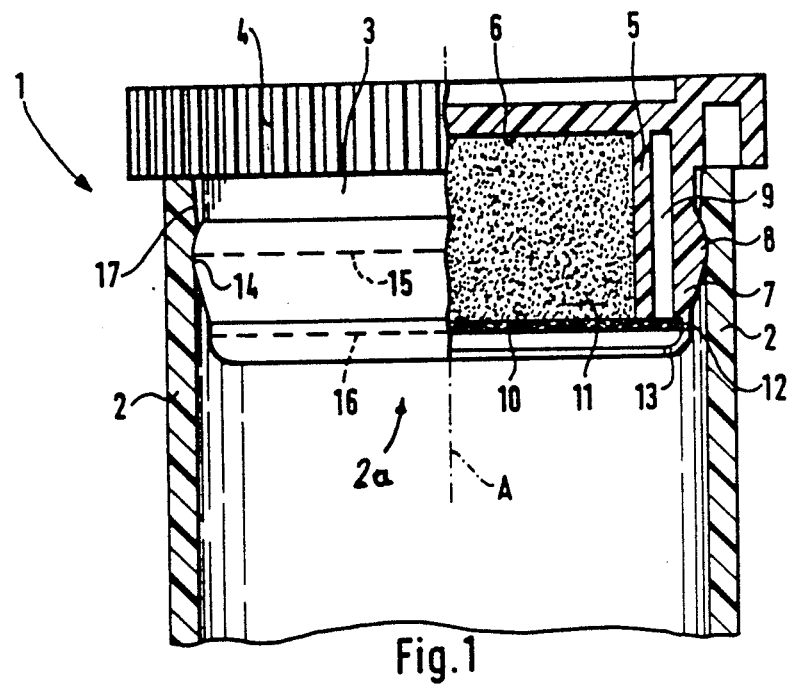
FIG. 1 is a vertical cross section through a container according to the present invention, the stopper being shown partly in section and partly in side view.

The test strip container, indicated as a whole by 1, comprises a cylindrically shaped container body 2 and a closure stopper 3 which closes the removal opening 2a of the container body.

The container body 2 is cylindrically shaped and its lower end, which is not illustrated in the Figures, is closed.

The stopper 3 is made of a synthetic resin, preferably polyethylene or polypropylene, by an injection moulding process. On a cover plate 4, the circumferential edge of which is, as usual, milled, is cast the cylindrically shaped wall 5 of the drying agent cell 6 and the substantially cylindrically shaped hollow plug 7 with a sealing beading 8. Between the outer side of the wall 5 and the inner side of the plug 7 an annular gap 9 is present.

The drying agent cell 6 is covered with a water vapour-permeable cardboard disc 10 toward the interior of the container. The cardboard disc 10 closes off not the drying agent cell 6, so that the drying agent 11 contained therein cannot fall out, and also serves as a support element for the hollow plug 7. On the lower end of the hollow plug 7, a reception groove 12 is preferably provided into which the cardboard disc 10 is placed during assembly of the stopper. It is then fixed by flanging of the projecting synthetic resin lip 13 by the action of heat.

The container is formed circularly symmetrically about the central axis A. The sealing beading 8 presses internally against a sealing surface 14 on the inner wall of the container body 2 oriented towards the axis A. The line of maximum extension of the sealing beading 8 is the zenithal line 15 illustrated by a broken line in FIG. 1. The cardboard disc 10 abuts the hollow plug 7 along the abutment line 16, which is also illustrated by a broken line.

Instead of the cardboard disc 10, some other support element can be used, such as an inserted spoked wheel. The lower end of the sealing beading 8 can also be made considerably thicker so that it acts as a support element. However, the illustrated embodiment is especially simple to manufacture and is practical to assemble.

It can clearly be seen from FIG. 1 that the cylindrical wall of the hollow plug 7 with the sealing beading 8 is, on the one hand, securely attached on its upper end with the cover plate 4 and, on the other hand, is braced in the region of its lower end on the support element 10. The support element is constructed so that, even in the slackened state of the stopper, it inwardly touches the hollow plug. In contradistinction thereto, the annular gap 9 between the plug 7 and the outer limit of the drying agent cell 6 is not closed even when the stopper is placed in the container body 2.

The action according to the present invention depends essentially on the fact that the hollow plug 7 can give way elastically radially inwardly in the region of the sealing beading 8 but, nevertheless, is dependably pressed outwardly by the bilateral mounting. The dimensions of the hollow plug thereby play a considerable part. In the case of a preferred embodiment, for a stopper with an external diameter of about 25 to 30 mm., there is used a hollow plug, the wall of which, in the cylindrical region, is about 1 mm. thick, the beading in the slackened state thereby projecting from the cylinder surface by about 1 mm.

For the function of the stopper, it is desirable for the zenithal line 15 of the sealing beading sealing a minimum distance in the axial direction not only from the cover plate 4 but also from the point on which the support element abuts (in the illustrated embodiment the abutment line 16). This minimum distance is, in every case, preferably at least 2 mm. and especially preferably at least 3 mm.

Above the sealing surface 14, i.e. towards the edge of the removal opening 2a, the container body 2 is narrowed. In the case of the embodiment illustrated in FIG. 1, the narrowing is formed by an annular beading 17, i.e. the upper edge of the container body 2 is continuously thickened inwardly. In this way, the open end of the container body 2 acheives an additional stability and the stopper 3 engages positively into the container body 2.

Figures 2, 3:
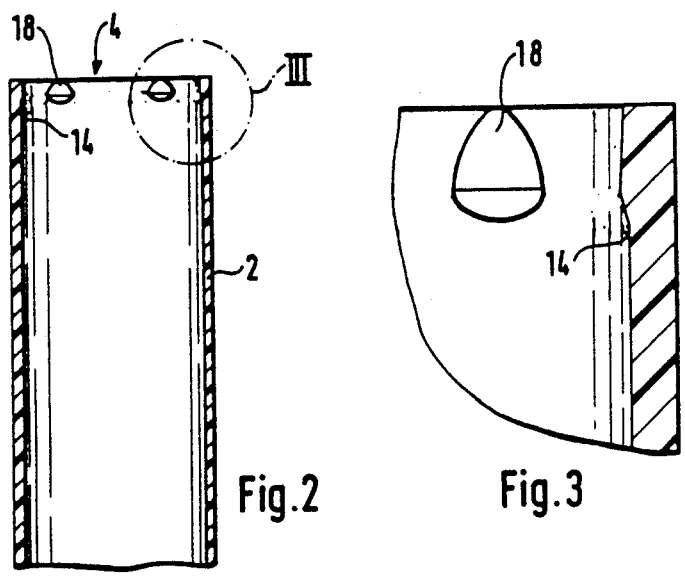
FIG. 2 is a section through a container body.
FIG. 3 is an enlarged view of section III in FIG. 2.

In FIGS. 2 and 3 of the accompanying drawings, there is illustrated an embodiment of the container body 2 in which the narrowing is realised in the form of a plurality of holding knops 18 which are formed on the inner side of the wall of the container body above the sealing surface 14. The holding knops 18 run flatly upwardly and downwardly. They permit an especially easy opening and closing of the container.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A container for test strips comprising:

a container body having a first end, a second end and an axis, said first end defining a circular opening and having a sealing surface facing the axis of the container;

stopper means for removably closing said circular opening, said stopper means having a cover plate, a hollow plug attached to the cover plate and extending into the container, said hollow plug having an inner and an outer side;

a sealing beading attached to the hollow plug and facing outwardly in a direction away from the axis, the sealing beading having a zenithal line corresponding to a maximum extension line which extends horizontally through the sealing beading relative to the axis, a drying agent cell located within the hollow plug; and support element means for supporting the hollow plug in the container, which support element means abuts against the inner side of the hollow plug in a region which is axially displaced away from the zenithal line toward the interior of the container;

the inner side of the hollow plug and an outer side of the drying agent cell defining an annular gap in the axial height of the sealing beading whereby the hollow plug is elastically deformable in an area of the sealing beading in a radial inward direction relative to the axis, said annular gap being maintained when the stopper means is in its container closing position.

2. The container according to claim 1, wherein the support means comprises a water vapour-permeable disc simultaneously covering the drying agent cell.

3. The container according to claim 2 wherein the hollow plug further comprises a flanged end facing away from the cover plate for reception of said disc.

4. The container according to claim 1, wherein the support element is axially displaced relative to the zenithal line of the sealing beading by at least 2 mm.

5. The container according to claim 4, wherein the support element is axially displaced relative to the zenithal line by at least 3 mm.

6. The container according to claim 1, wherein the circular opening narrows on at least a part of its circumference with regard to a diameter of the sealing surface in a direction away from the second end of the container.

7. The container according to claim 6, wherein the first end of the container comprises a continuous annular beading to thereby narrow the circumference part of the circular opening.

8. The container according to claim 6, wherein the first end of the container comprises a plurality of holding knops to thereby narrow the circumference part of the circular opening.

* * * * *